(12) United States Patent
Halstrom

(10) Patent No.: US 7,448,388 B2
(45) Date of Patent: Nov. 11, 2008

(54) MANDIBLE POSITIONING DEVICES

(76) Inventor: Leonard W. Halstrom, 140 Isleview Place, Lions Bay, British Columbia (CA) V0N 2E9

( * ) Notice: Subject to any disclaimer, the term of this patent is extended or adjusted under 35 U.S.C. 154(b) by 147 days.

(21) Appl. No.: 10/635,483

(22) Filed: Aug. 7, 2003

(65) Prior Publication Data
US 2005/0028827 A1    Feb. 10, 2005

(51) Int. Cl.
*A61F 5/56* (2006.01)
(52) U.S. Cl. .................................. 128/861; 602/902
(58) Field of Classification Search ................ 128/848, 128/861, 859, 860, 862; 433/68, 69, 140, 433/6, 19; 602/902
See application file for complete search history.

(56) References Cited

U.S. PATENT DOCUMENTS

| | | | | |
|---|---|---|---|---|
| 4,602,905 A | * | 7/1986 | O'Keefe, III | 433/41 |
| 5,090,901 A | * | 2/1992 | Levandoski | 433/56 |
| 5,409,017 A | | 4/1995 | Lowe | |
| 5,683,244 A | * | 11/1997 | Truax | 433/6 |
| 5,816,799 A | * | 10/1998 | Parker | 433/6 |
| 5,826,579 A | | 10/1998 | Remmers et al. | |
| 5,921,942 A | | 7/1999 | Remmers et al. | |
| 6,012,920 A | * | 1/2000 | Woo | 433/19 |
| 6,109,265 A | * | 8/2000 | Frantz et al. | 128/848 |
| 6,255,262 B1 | * | 7/2001 | Keenan et al. | 508/486 |
| 6,273,859 B1 | | 8/2001 | Remmers et al. | |
| 6,286,508 B1 | | 9/2001 | Remmers et al. | |

OTHER PUBLICATIONS

Lowe, Alan A., "Dental Appliances for the Treatment of Snoring and Obstructive Sleep Apnea", Chapter 69, pp. 722-725 of "Principles and Practice of Sleep Medicine" by W. B. Saunders, 1994.

* cited by examiner

*Primary Examiner*—Patricia Bianco
*Assistant Examiner*—Camtu Nguyen

(57) ABSTRACT

A mandible positioning device or pharyngeal airway adjuster has upper and lower bite blocks and a connection between the upper and lower bite blocks, the connection being manually adjustable for displacing the lower bite block relative to the upper bite block. The adjustable connection protrudes forwardly from the upper and lower bite blocks so that, in use of the device, the manually adjustable member is located and accessible in front of a patient fitted with the mandible positioning device. The manually adjustable connection has screws which are adjustable independently of one another for effecting relative horizontal and vertical displacement, respectively, of the upper and lower bite blocks.

2 Claims, 3 Drawing Sheets

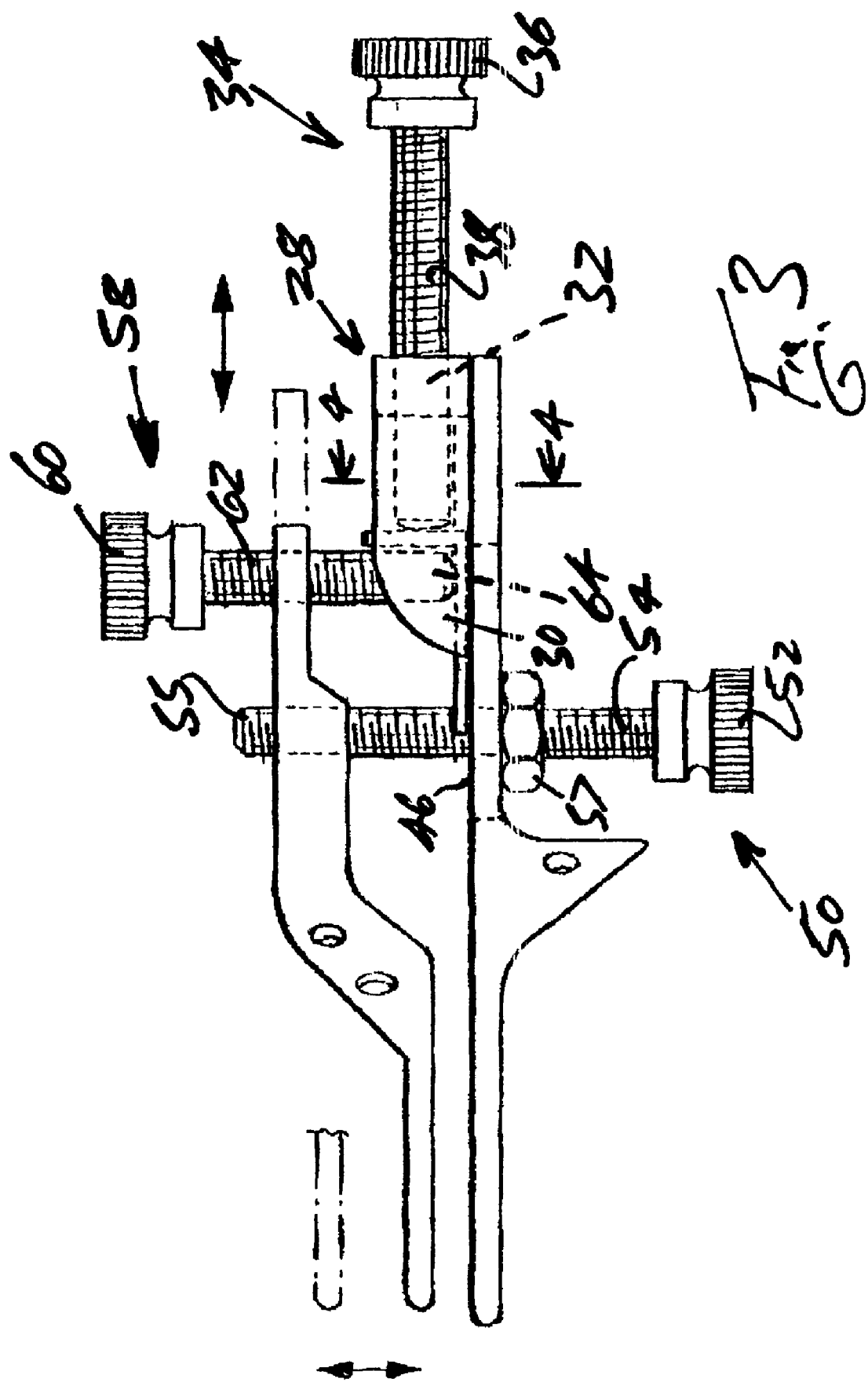

MANDIBLE POSITIONING DEVICES

BACKGROUND OF THE INVENTION

1. Field of the Invention

The present invention relates to mandible positioning devices for use as pharyngeal airway adjusters.

2. Description of the Related Art

In patients who are suffering from the sleep disorder known as obstructive sleep apnea, the flesh and muscles of the tongue and throat relax, as the patients attempt to sleep, so that the pharyngeal airway is blocked and, consequently, the patients briefly stop breathing. When this occurs, the patients are awakened by the consequent lack of oxygen and blood, which often occurs with a loud snort or a bodily jerk.

For the proper diagnosis and treatment of patients subject to sleep apnea, polysomnographic testing of the patients is performed in sleep centers or in the patients' homes, while the patients are asleep, to record various factors, including the oxygen level in the patients' blood, the heart action, chest and abdominal movements and brain activity of the patients.

It has previously been proposed to provide a dental device for adjustably displacing the mandible of a patient in horizontally and vertically, relative to the maxillary dentition of the patient, in order to thereby increase the pharyngeal airway size of the patient so as to counteract such blockage as caused in the above-described manner.

It has been found that the displacement of the mandible in a forward, i.e. horizontal, direction relative to the maxillary dentition and, also, in a downward, i.e. vertical, direction away from the maxillary dentition should be adjusted, while the patient is being tested, in order to determine the optimum positioning of the mandible.

In U.S. Pat. No. 5,409,017, issued Apr. 25, 1995, to Lowe, there is disclosed a mandible positioning device having upper and lower bite blocks, which fit onto and engage the maxillary and mandibular dentition of a patient, with an adjustable connection between the upper and lower bite blocks. This connection allows the position of the lower bite block to be adjusted forwardly and rearwardly, i.e. horizontally, relative to the upper bite block, in order to thereby adjust the relative positions of the upper and lower bite blocks and to adjust correspondingly the position of the patient's mandible.

It is, however, a disadvantage of this prior device that the connection is located between the upper and lower bite blocks and, therefore, is not accessible while the device is installed in the mouth of a patient. In order to adjust the device, it is necessary to withdraw the device from the patient's mouth.

A further disadvantage of this prior device is that it does not allow the spacing between the upper and lower bite blocks to be adjusted.

BRIEF SUMMARY OF THE INVENTION

It is accordingly an object of the present invention to provide a novel and improved mandible positioning device having upper and lower bite blocks which can be manually adjusted in position relative to one another while the device is installed in the mouth of a patient.

It is a further object of the present invention to provide a manually adjustable mandible positioning device which allows a lower bite block to be adjusted forwardly relative to an upper bite block and which also allows the vertical spacing between the upper and lower bite blocks to be adjusted.

According to the present invention, there is provided a mandible positioning device comprising upper and lower bite blocks and a manually adjustable connection interconnecting the upper and lower bite blocks for displacing the upper and lower bite block relative to one another, the manually adjustable connection protruding forwardly from the upper and lower bite blocks so that, in use of the mandible positioning device, the manually adjustable connection is located in front of a patient fitted with the mandible positioning device. The manually adjustable connection can therefore be adjusted while the device remains in the mouth of a patient.

Consequently, when the present mandible positioning device is in use, the position of the lower bite block can be adjusted, for example in a clinical setting while the patient is awake and in order to allow visual inspection of the patient's airway, e.g. to determine the optimum relative positions of the upper and lower bite blocks to counteract snoring. By locating the manually adjustable connection forwardly of the upper and lower bite blocks, the space between the upper and lower bite blocks, within the patient's mouth, can be left unobstructed by these members, which facilitates such visual inspection.

Another use of the present invention is to enable relative adjustment of the upper and lower bite blocks while the patient fitted with the device according to the present invention is unconscious, e.g. in a post-operative state, or otherwise incapacitated, in order to contract sleep apnea.

The manually adjustable connection may comprise a pair of independently manually adjustable members controlling, respectively, forward or horizontal displacement of the lower bite block and the spacing, or vertical spacing, between the upper and lower bite blocks.

The pair of manually adjustable members preferably comprise a first adjustment screw having a longitudinal axis extending forwardly from the mandible positioning device for horizontal adjustment, and a second adjustment screw, having a longitudinal axis perpendicular to the longitudinal axis of the first-mentioned adjustment screw, for vertical adjustment.

BRIEF DESCRIPTION OF THE DRAWINGS

The invention will be more readily understood from the following description of a preferred embodiment thereof, given by way of example, with reference to the accompanying drawings, in which:

FIG. 3 shows a view taken in side elevation of the device of FIG. 1.

DESCRIPTION OF THE PREFERRED EMBODIMENT

Figure 1:
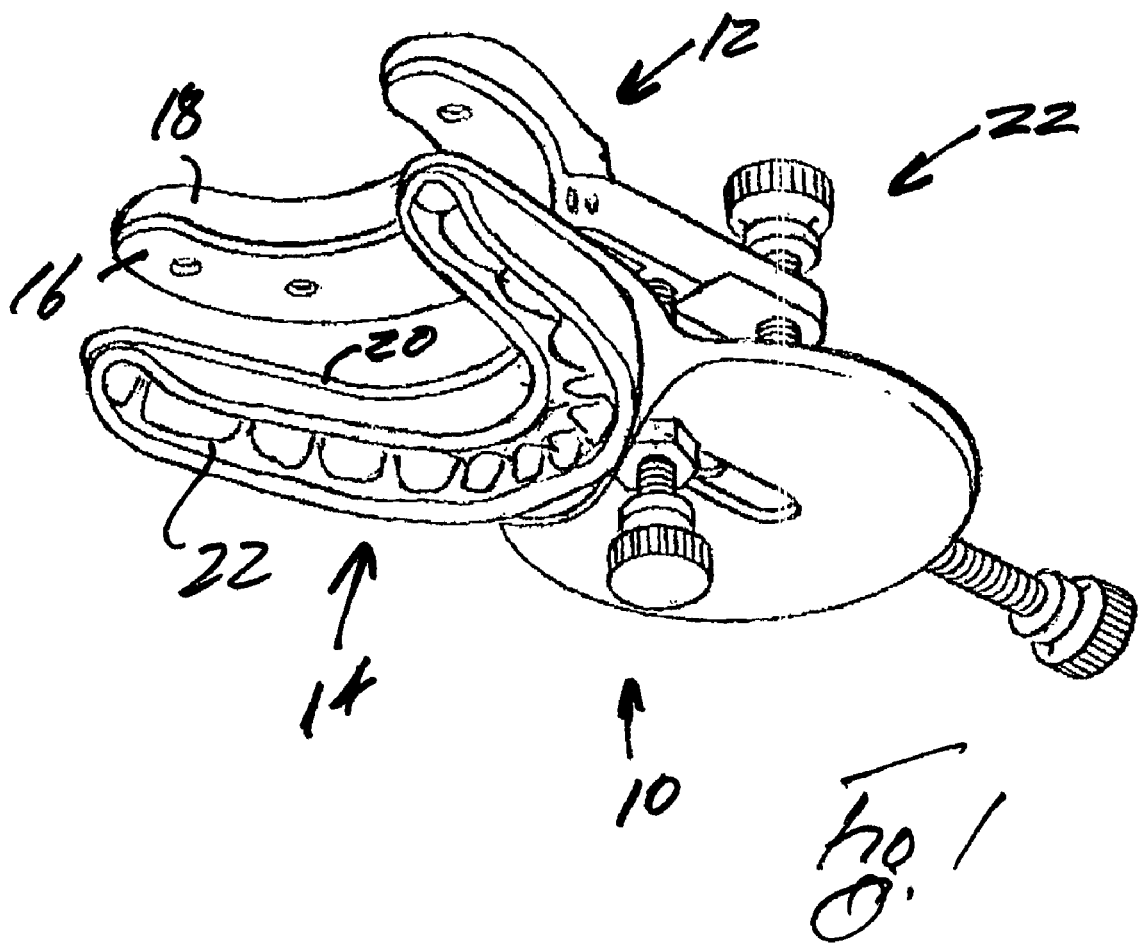
FIG. 1 shows a view taken in perspective from below of a mandible positioning device embodying the present invention.

The mandible positioning device shown in FIG. 1 is indicated generally by reference numeral 10 and comprises a maxillary dentition engagement component or upper bite block indicated generally by reference numeral 12 and a mandibular dentition engagement component or lower bite block indicated generally by reference numeral 14.

More particularly, the upper bite block 12 comprises a flat U-shaped plate or tray 16 with a dental molding 18, shaped to interfit with the maxillary dentition of a patient, and the lower bite block comprises a U-shaped inverted tray 20 carrying, at its underside, a dental molding 22 shaped for interengagement with the mandibular dentition of the patient.

The upper and lower bite blocks 12 and 14 are interconnected by a manually adjustable connection indicated generally by reference numeral 22, which projects forwardly from the upper and lower bite blocks 12 and 14 so as to protrude beyond the mouth and lips of a patient (not shown). The manually adjustable connection 22 is therefore accessible at the exterior of the patient's mouth while the device remains fitted to the patient with the upper and lower bite blocks 12 and 14 in engagement with the patient's dentition.

Figure 2:
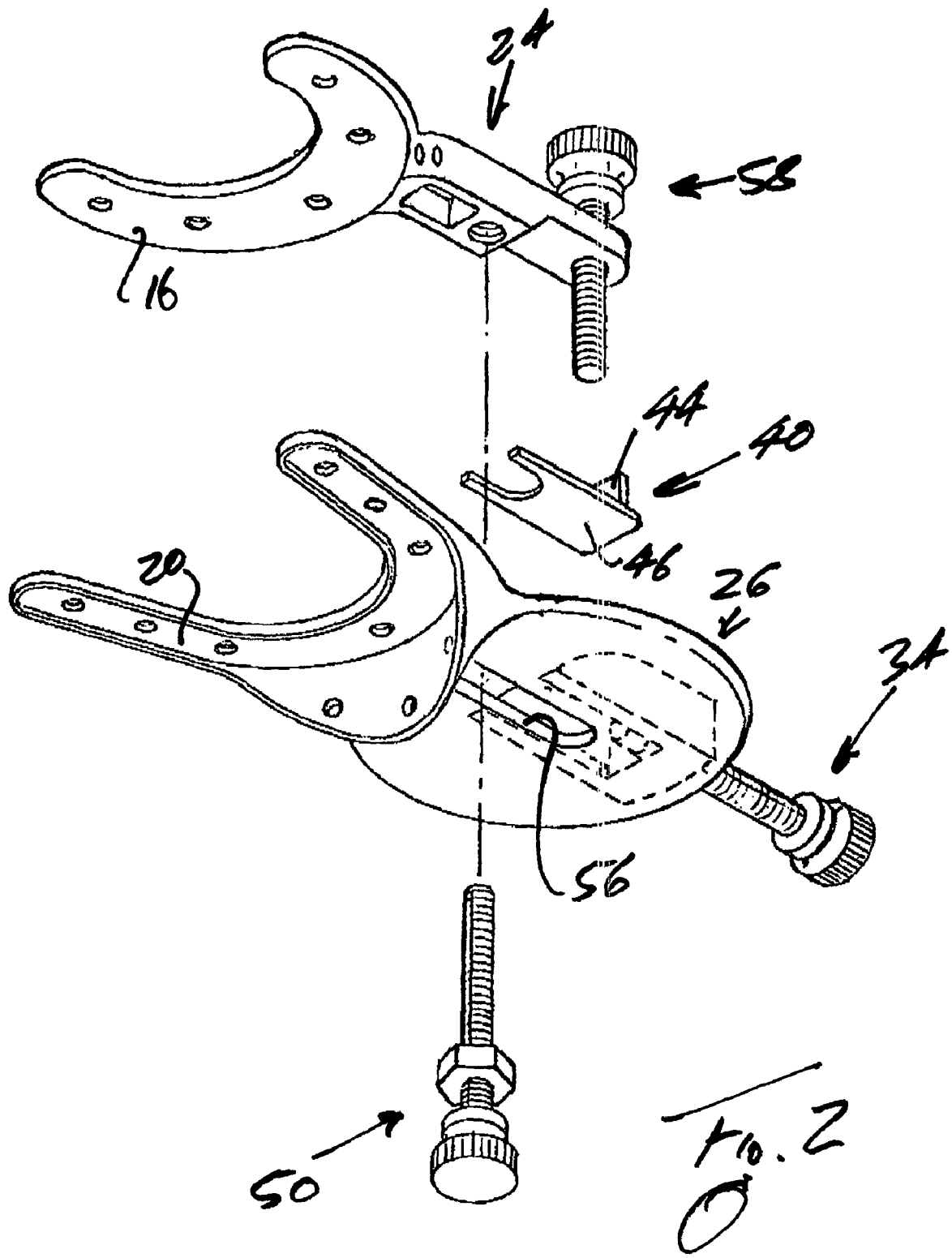
FIG. 2 shows an exploded view, taken in perspective from below, of components of the device of FIG. 1.

The adjustable connection 22 includes a projection, indicated generally by reference numeral 24 in FIG. 2, which protrudes forwardly from the upper bite block tray 16, and a disc-shaped projection, indicated generally by reference numeral 26, which protrudes forwardly from the lower bite block tray 20.

The disc-shaped projection 26 is formed, on its upper surface, with an upwardly-open formation, indicated generally by reference numeral 28 in FIG. 3. The formation 28 has parallel side walls 30 and, at the forward end of the formation 28, an end wall 32 extending between the side walls 30.

A first manually adjustable member or adjustment screw, indicated generally by reference numeral 34, has a knurled head 36 and a threaded shank 38. The threaded shank 38 extends through and in threaded engagement with an opening in the end wall 32 of the formation 28, with the longitudinal axis of the shank 38 extending forwardly and rearwardly of the device 10.

The rear end of the shank 38, opposite from the knurled head 36, abuts a slide member, which is indicated generally by reference numeral 40 in FIG. 2.

The slide member 40 comprises a vertical end flange 42, extending vertically upwardly from a horizontal slide plate 44.

Figure 4:
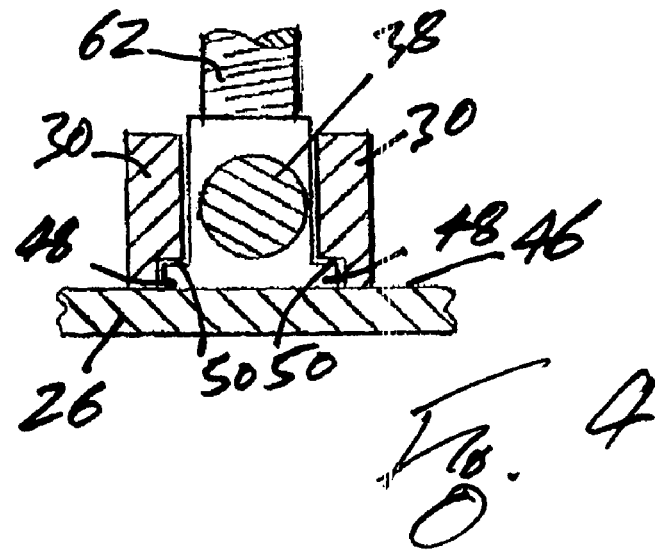
FIG. 4 shows a broken-away view, taken in cross-section along the line 4—4 of FIG. 3.

The slide plate 44 is slidably supported on an upper surface 46 of the disc-shaped projection 26 and, as shown in FIG. 4, has opposite longitudinal marginal end portions 48 engaged in recesses 50 formed in opposed faces of the side walls 30 adjacent the upper surface 46 of the disc-shaped projection 26.

The upper and lower projections 24 and 26 are interconnected by a second manually adjustable member or adjustment screw, which is indicated generally by reference numeral 50 in FIG. 3 and which has a vertical longitudinal axis extending perpendicular to the horizontal longitudinal axis of the first adjustment screw 34.

The second adjustment screw 50 has a knurled head 52 and a shank 54 which extends upwardly from the head 52 through a slot 56 in the disc-shaped projection 26, the shank 54 having an upper end 55 which extends through and in threaded engagement with an opening in the upper projection 24. A nut 57 on the shank 54 of the second adjustment screw 50 underlies the disc-shaped projection 26.

A third manually adjustable member or adjustment screw, indicated generally by reference numeral 58, has a knurled head 60 and a shank 62 extending downwardly from the knurled head 60, the shank 62 being parallel to the shank 54 of the second adjustment screw 50 and, thus, having a longitudinal axis perpendicular to that of the first adjustment screw 34.

A lower end 64 of the shank 62 of the adjustment screw 58 abuts the upper surface of the slide plate 46 of the slide member 40.

By rotation of the first adjustment screw 34 relative to the formation 28, the slide member 40 can be urged to the left, as viewed in FIG. 3, relative to the formation 28. The slide plate 44 of the slide member is thereby pressed against the shank 62 of the adjustment screw 58, so that the formation 28 and, therewith, the disc-shaped projection 26 and the lower bite block 14 are displaced to the right, as viewed in FIG. 3, relative to the adjustment screw 58, the upper projection 24 and the upper bite block 12.

During this displacement, the shank 54 of the second adjustment screw 50 is correspondingly displaced along the slot 56 formed in the disc-shaped projection 26.

In this way, the lower bite block 14 can be adjustably displaced relative to the upper bite block 12 in a forward or horizontal direction, parallel to a horizontal plane between the upper and lower bite blocks 12 and 14.

To adjustably increase the vertical spacing of the upper and lower bite blocks 12 and 14, the nut 57 is firstly loosened from the disc-shaped projection 26, and the second adjustment screw 50 is then rotated to permit corresponding displacement of the disc-shaped lower projection 26 and, therewith, the lower bite block 14 downwardly relative to the upper projection 24 and the upper bite block 12 and perpendicular to the above-mentioned horizontal plane.

When this vertical displacement has been completed, to an extent which is determined by the position of the nut 57 along the shank 54 of the second adjustment screw 50, the adjustment screw 58 is rotated to press downwardly onto the slide member 46 and, thereby, to press the disc-shaped lower projection 26 against the nut 57.

The first and second adjustment screws 34 and 58 are thus adjustable independently of one another for adjusting the forward displacement and the vertical spacing, respectively, of the lower bite block 14 relative to the upper bite block 12.

As will be apparent to those skilled in the art, various modifications may be made in the above-described embodiment of the present invention within the scope of the appended claims.

For example, while the above-described embodiment of the invention employs adjustment screws for adjusting the relative positions of the upper and lower bite blocks 12 and 14, it is envisaged that other means, for example spring-actuated detents, could be employed for this purpose.

I claim:

1. A mandible positioning device, comprising upper and lower bite blocks and an adjustable connection interconnecting said upper and lower bite blocks, said adjustable connection including first and second manually adjustable screws for displacing said lower bite block relative to said upper bite block and said adjustable connection protruding forwardly from said upper and lower bite blocks so that, in use of said mandible positioning device, said manually adjustable connection is located in front of a patient fitted with said mandible positioning device:

wherein said first manually adjustable screw controls displacement of said lower bite block forwardly relative to said upper bite block;

wherein said second manually adjustable screw controls displacement of said upper and lower bite blocks towards and away from one another; and wherein said adjustable connection comprises first and second forward projections extending from said upper and lower bite blocks, respectively, said first manually adjustable screw having a longitudinal axis extending forwardly from said mandible positioning device, and said second manually adjustable screw having a longitudinal axis perpendicular to the longitudinal axis of said first manually adjustable screw.

2. A mandible positioning device as claimed in claim 1, wherein said adjustable connection device includes a third screw having a longitudinal axis parallel to the longitudinal axis of said second manually adjustable screw, and a locknut on said third screw.

* * * * *